United States Patent [19]

Eichel et al.

[11] Patent Number: 4,983,401

[45] Date of Patent: Jan. 8, 1991

[54] SUSTAINED RELEASE PHARMACEUTICAL PREPARATIONS HAVING PH CONTROLLED MEMBRANE COATINGS

[75] Inventors: Herman J. Eichel; Brent D. Massmann, both of Columbus, Ohio

[73] Assignee: Kinaform Technology, Inc., Dayton, Ohio

[21] Appl. No.: 354,105

[22] Filed: May 22, 1989

[51] Int. Cl.$^5$ .................. A61K 9/24; A61K 9/16; A61K 9/50; A61K 9/54
[52] U.S. Cl. .................. 424/473; 424/458; 424/494; 424/490; 424/497
[58] Field of Search ............... 424/473, 494, 490, 497, 424/458

[56] References Cited

U.S. PATENT DOCUMENTS

| | | | |
|---|---|---|---|
| 3,155,590 | 11/1964 | Miller et al. | 424/495 |
| 3,341,416 | 9/1967 | Anderson et al. | 424/495 |
| 3,488,418 | 2/1970 | Holliday et al. | 424/464 |
| 3,492,397 | 1/1970 | Peters et al. | 424/495 |
| 3,531,418 | 9/1970 | Fanger et al. | 427/213.3 |
| 3,878,276 | 4/1975 | Hoernschemeyer | 264/41 |
| 4,025,613 | 5/1977 | Guy et al. | 424/472 |
| 4,083,949 | 4/1978 | Benedikt | 424/19 |
| 4,205,060 | 5/1980 | Monsimer et al. | 424/14 |
| 4,305,823 | 12/1981 | Batzer et al. | 210/500.2 |
| 4,377,481 | 3/1983 | Jakabhazy | 210/500.2 |
| 4,663,050 | 5/1987 | Li et al. | 210/649 |

FOREIGN PATENT DOCUMENTS

| | | |
|---|---|---|
| 77956 | 5/1983 | European Pat. Off. |
| 108269 | 6/1978 | Japan. |
| 11687 | 4/1981 | Japan. |

*Primary Examiner*—Merrell C. Cashion, Jr.
*Assistant Examiner*—G. S. Kishore
*Attorney, Agent, or Firm*—Kilworth, Gottman, Hagan & Schaeff

[57] ABSTRACT

A sustained-release pharmaceutical preparation utilizing a pH controlled diffusion membrane composed of a pH sensitive film-forming polymer. The film forming polymer may be an enteric polymer containing phthalic acid with one carboxyl group attached to the enteric polymer via an ester bond, and the second carboxyl group remaining a free acid so that the modified film forming polymer is hydrophobic at low pH and hydrophilic at higher pH. Hydrophobic stearyl side chains are attached to the enteric polymer which causes the pH controlled diffusion membrane to remain insoluble at high pH. Alternatively, the pH sensitive film forming polymer may be a polymer containing hydrophobic and free acid groups so that the modified film forming polymer is hydrophobic at low pH and hydrophilic but insoluble at high pH. In the preferred sustained-release pharmaceutical preparation the film forming polymer is coated onto core drug particles to produce a pH controlled diffusion membrane surrounding the core drug and form microparticles which may be admixed with free drug or time-release drug and placed in a gelatin capsule or tabletted.

23 Claims, No Drawings

SUSTAINED RELEASE PHARMACEUTICAL PREPARATIONS HAVING PH CONTROLLED MEMBRANE COATINGS

BACKGROUND OF THE INVENTION

The present invention relates to oral sustained release pharmaceutical preparations in the form of microparticles of core drug particles surrounded by a pH controlled diffusion membrane.

As is well known, the maximum time of effectiveness in many pharmaceutical preparations, particularly those containing a drug such as aspirin, acetaminophen, propranolol, and dextromethorphan, etc. is only a few hours because of biological modification and/or elimination of the medication in the body. Consequently repeated dosages must be taken at frequent intervals to obtain long term therapeutic levels of drug. Furthermore, these drugs usually dissolve readily in the digestive juices and the total dosage is immediately fed into the blood stream. After high initial peak concentrations, the level of drug in the blood stream constantly decreases because of the biological elimination, so there is little or no therapeutic effect at the end of the period between dosages. As a result, the therapeutic effect fluctuates between dosages corresponding to the peaks and valleys in the level of drug in the blood as commonly measured by trough to peak ratios.

One common approach in attempting to provide a more constant drug level is to microencapsulate aspirin, for example, with a capsule wall material which provides a slower dissolution rate than free aspirin. The early work in that regard is represented by U.S. Pat. Nos. 3,155,590; 3,341,416; 3,488,418, and 3,531,418. Those patents, among others, disclose dispersing particles of aspirin in hot cyclohexane solution containing ethyl cellulose and then introducing a phase-separation inducing agent, such as butyl rubber or polyethylene. Upon cooling, the aspirin particles become coated with ethyl cellulose. The coated particles are then admixed with tabletting excipients and formed into dosage-sized tablets. When ingested, the tablets disintegrate rapidly and the individual particles of encapsulated aspirin are dispersed in the stomach. The gastric juices slowly diffuse through the capsule walls, dissovle the aspirin, and the dissolved aspirin slowly diffuses or leaches out through the capsule walls into the body. Although the resultant blood level content is sustained to a measurable extent, the aspirin is diffused into the body rapidly enough so there is an initially high blood level content which decreases quite rapidly within a few hours. These dissolution properties yield undesirable blood aspirin concentration versus time curves.

Guy U.S. Pat. No. 4,025,613 discloses a multi-layered tablet. One layer comprises aspirin coated with cellulose acetate phthalate and the other layer is free aspirin. With multi-layered microencapsulated particles, as discussed above, the dissolution rate decreases rapidly and the blood aspirin concentration at 2-3 hours must greatly exceed the therapeutic level in order to maintain adequate aspirin concentrations at 8 hours. As a result, efforts have been made to adjust the rate of dissolution and thus, control the timing of sustained drug release. See for example, Peters U.S. Pat. No. 3,492,397 where the dissolution rate is said to be controlled by adjusting the wax/ethyl cellulose ratio of the applied spray coating. See also U.S. Pats. No. 4,205,060 and 3,488,418 where it is indicated that the rate of dissolution can be controlled by varying the thickness of the coating.

Another method for providing an encapsulated pharmaceutical composition is discussed in published European patent application No. 77,956, published May 4, 1983. EPO Publication No. 77,596 discloses the use of microcapsules containing a coated core material such as pharmaceutical compounds and foodstuffs. The coating is applied by dispersing the core material into a solution containing ethyl cellulose as the wall-forming material. A phase separation of the ethyl cellulose from the dispersion of core material is carried out by cooling the dispersion. During this cooling, an enteric polymer material is incorporated into the ethyl cellulose coating walls by adding the enteric polymer material with stirring while the ethyl cellulose is still in the "gel" state. The enteric polymer material thus added penetrates, and is dispersed into the coating walls. When the microcapsules are administered, the release of the active compound does not generally occur in the stomach. However, the enteric polymer material is easily dissolved in the intestinal tract, thereby making the microcapsules porous. The porosity of the microcapsules promotes the rapid release of the active compound in the intestinal tract.

A similar approach is found in Japanese Patent Publication No. 12614/81 published Mar. 23, 1981. Japanese Publication No. 12614/81 discloses an enteric protective coating composition which will not readily dissolve in acidic gastric juices, but rapidly (within minutes) dissolves at the pH found in the intestines. The enteric coating is an aqueous dispersion of, for example. hydroxy propyl methyl cellulose phthalate, a gelling agent such as diacetin, and hydroxy propyl methyl cellulose. See, also. Japanese Patent Publication No. 11687/81, published Mar. 16, 1981, which uses hydroxy propyl methyl cellulose phthalate as an enteric coating.

The systems described in the EPO Japanese Publications are essentially "delayed" release mechanisms. There is a delay of medicament release in the stomach, but once the coated medicament reaches the intestines, the release of medication is rapid. There is no sustained-release of medication in the intestines. Furthermore, these systems use a "mixed" wall material which result in processing difficulties.

Finally reference is made to applicants' copending, application Ser. No. 017,988, filed Feb. 24, 1987. the disclosure of which is hereby incorporated by reference. In the copending application there is disclosed a sustained-release pharmaceutical preparation comprising a dual walled coated drug having an inner wall microencapsular control coating, such as ethyl cellulose, and an outer wall enteric coating, such as ethyl cellulose, and an outer wall enteric coating, such as cellulose acetate phthalate. Such a dual-walled material will release less than 10% per hour of core drug while in the stomach but will slowly release the core drug in the intestines to provide adequate drug levels for 8 or more hours. While this represents an improved result, film forming polymers designed to have permeability controlled by pH will provide increased flexibility in designing drug release profiles and will make processing easier and more economical by eliminating the need for a dual wall structure.

Thus, there remains a need for a film forming polymer with a permeability controlled by pH which can be used to coat core drug particles and produce microparticles which provide a delayed and sustained-release of drug.

SUMMARY OF THE INVENTION

The present invention meets those needs by providing a sustained release pharmaceutical preparation utilizing a film forming polymer which has its permeability pH controlled. This film forming polymer is used to form a pH controlled diffusion membrane. The pH controlled diffusion membrane is particularly used as a coating on core drug particles to produced sustained release pharmaceutical microparticles.

The preferred film forming polymer comprises an enteric polymer such as a cellulose acetate phthalate (CAP) which has been modified to render it insoluble at intestinal pH, or an insoluble diffusion barrier such as a methacylic/acrylic acid ester copolymer (MAA) which has been modified to render it pH sensitive.

The CAP enteric polymer contains phthalic acid with one carboxyl group attached by an ester bond to the cellulose backbone and the second carboxyl group remains a free acid so that the film forming polymer is hydrophobic at low pH and hydrophilic and soluble at a higher pH. Upon modification, the modified film forming polymer includes hydrophobic stearyl side chains attached to the enteric polymer which causes the polymer to remain insoluble at higher pH. The permeability of the modified polymer is a function of pH.

The modified MAA polymer includes acid groups which partially replace the ester groups. The polymer forms films of low permeability at low pH but the permeability increases at higher pH because the acid groups are converted to the more hydrophilic salt.

Other film forming polymers may also be used as long as they have certain characteristics when used to coat a core drug particles. The preferred characteristics of the film forming polymer must be non-toxic, must have film forming ability, a moity that changes from hydrophobic at low pH to hydrophilic at neutral or alkaline pH. and sections which maintain the film intact at neutral and alkaline pH.

In addition to the modified CAP mentioned above, cellulose acetate trimellitate, hydroxylethyl cellulose ephthalate, cellulose acetate tetrohydrophthalate, hydroxypropylmethyl cellulose phthalate and polyvinyl acetate phthalate may be modified by attachment of hydrophobic side chains such as long chain fatty acids so that they form films with low permeability in acidic envirionments but remain intact but have higher permeability at alkaline or neutral pH.

Likewise, in addition to the modified MAA mentioned above polyethylene maleic anhydride, polystyrene maleic anhydride and other related co-polymers can also be formulated into film forming polymers which preferably have their permeability pH controlled. Acid groups which are hydrophobic at low pH and hydrophilic at neutral pH are formed from the acid anhydride groups contained in these polymers. The hydrophobic copolymer subunits keep the film intact at neutral or alkaline pH.

The sustained-release pharmaceutical preparation of the present invention uses the pH controlled, single coat, diffusion membrane. Preferably the sustained release pharmaceutical preparation is in the form of multi units of microparticles of core drug particles surrounded by a pH controlled diffusion membrane. The pH controlled diffusion membrane is formed by coating a pH sensitive film forming polymer of the present invention onto core drug particles. Because the permeability of the membrane is pH controlled, it will not release significant amounts of the core drug in the stomach (where a low pH is encountered) but will slowly and steadily release the drug in the intestines (where a higher pH is encountered).

The core drug should be one which is reasonably soluble in the digestive fluids so as to be slowly releasable in the intestines through the control membrane. Preferred are aspirin, acetaminophem, diphenhydramine hydrochloride, propranolol hydrochloride, dextromethorphen hydrobromide, disopyramide phosphate and furosemide. Other usable drugs soluble in the digestive fluids include various vitamins, minerals, antibotics, and other widely used drugs. The preferred size range of drug core is from about 100 to about 2000 microns in diameter, more preferably around 500 to 1200 microns. The drug core may be drug layered onto non-pareil seeds, crystals of drug, granulated drug powder, or any other coatable particles which contain drug.

The pH controlled diffusion membrane is preferably applied by a spray coating process. The coating level of the core drug particles with the modified film forming polymer is preferably from approximately 3% to 30% of total weight depending on the core size and drug solubility resulting in a pH controlled diffusion membrane thickness of about 5 to 100 microns. The total microparticle diameter is around 110 to 2200 microns. Multi-units of these microparticles are combined in a gelatin capsule or pressed into a tablet to achieve the desired dosage level.

The multi-unit microparticles may also be admixed or concentrically coated with other fractions of free and/or time-release drug. The admixture may be placed in either capsules or tablets along with other usual ingredients such as binders, fillers, lubricants, etc. In this form free drug is released immediately in the stomach. The drug having the pH controlled diffusion membrane does not release drug in the stomach; but rather, in the intestines. The drug is released slowly and steadily from the pH controlled diffusion membrane coated portion of the admixture by reason of the mechanism discussed above. The admixture, thus, provides for both immediate and delayed sustained release of the drug.

Whether the microparticles of the present invention are packaged with free drug or not, the follow benefits are obtained by use of multi-units of these microparticles:

(a) There is a more uniform and longer sustained release of the drug because each microparticle acts individually and is dispersed throughout the gastrointestinal tract to give a statistically beneficial release.

(b) potential irritation of the gastrointestinal tract by the drug is minimized because of the small, localized, individual release by each microparticle, and (c) The danger of overdosing due to the "burst", "surge" or "dump" effect known to occur with large non-sustained-release dosages or premature release of sustained-release dosages due to defects, is virtually eliminated because the small, individually-releasing microparticles ensure sustained statistical release. A premature release by a defective microparticle is insignificant since each microparticle is only a fraction of the total drug dosage.

Accordingly, it is an object of the present invention to provide a sustained-release pharmaceutical preparation having a pH controlled diffusion membrane coated on a core drug. These and other objects and advantages of the invention will become apparent from the following description of the preferred embodiments and the appended claims.

DESCRIPTION OF THE PREFERRED EMBODIMENT

In one embodiment the preferred pH sensitive film forming polymer of the present invention is a cellulose acetate phthalate (CAP) with attached hydrophobic stearyl side chains. This enteric polymer, cellulose acetate phthalate, is modified in this preferred manner to remain insoluble at neutral or alkaline pH and to have its permeability pH controlled.

Other enteric film forming polymers which may be used include cellulose acetate trimellitate, hydroxypropylmethyl cellulose phthalate and polyvinyl acetate phthalate. These polymers may also be modified by attachment of hydrophobic side chains such as long chain fatty acids so that they form films with low permeability in acidic environments and remain intact but have higher permeability at neutral or alkaline pH.

In another preferred embodiment the film forming polymer is a methacrylic acid/acrylic acid ester copolymer (MAA). Methacrylic/acrylic acid ester copolymers with a mean molecular weight of 800,000 are commonly used as a low permeability pH independent diffusion barrier for sustained release pharmaceutical preparations. The chemical structure of the polymers used is:

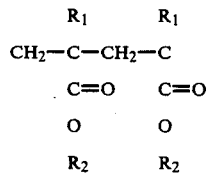

Where $R_1$ is —H or —$CH_3$ and $R_2$ is —$CH_3$ or —$C_2H_5$.

The replacement of a portion of the ester groups in this structure with acid groups produces a polymer which forms films of low permeability at low pH but the permeability increases at higher pH because the acid groups are converted to the more hydrophilic salt.

Other copolymers of acidic monomers and hydrophobic monomers which may be used include polyethylene maleic anhydride, polystyrene maleic anhydride and other related polymers. Acid groups which are hydrophobic at low pH and hydrophilic at neutral pH form from the acid anhydride units in these polymers. The hydrophobic units keep the film intact at neutral or alkaline pH.

The preferred pH sensitive film forming polymers are preferably coated onto core drug particles to produce the preferred sustained release pharmaceutical preparation. Examples of drugs which may be used as the core drug include most preferrably aspirin acetaminophen, diphenhydramine hydrochloride propranolol hydrochloride, furosemide disopyramide phosphate, and dextromethorphan hydrobromide. In addition to these classes of drugs, others may also be used. For example, vitamins, minerals. antibiotics, and analgesics may be used as the core drug. As long as the drug has sufficient solubility to be releasable in the intestines through the pH controlled diffusion membrane, is or can be made from about 100 to about 2000 microns in diameter, and is capable of having the modified film forming polymer of the present invention applied to the drug particles, it is usable.

The preferred process for applying the pH sensitive film forming polymer to the core drug is a fluid bed spray coating process. The coating level of film forming polymer to core drug is preferably from approximately 3 to 30% and more preferably from about 5 to 20%. The result is a pH controlled diffusion membrane with a thickness of approximately 5 to 100 microns. A total microparticle size of about 110 to 2200 microns is achieved.

Because the permeability of the membrane is pH controlled, it will not release significant amounts of the core drug in the stomach, but will slowly and steadily release the drug in the intestines. The drug release profile is controlled by the magnitude of the pH controlled change in permeability and the thickness of the control membrane formed from the pH sensitive film forming polymer. Generally, it is desirable that 0 to 15% of the core drug be released from the microparticles at pH 1.1 in 2 hours and that 80 to 100% be released at pH 6.0-7.5 in 6-24 hours. Such release rates are illustrated by the examples set forth below.

EXAMPLE I 15.0 grams Eastman C-A-P from Eastman Chemical Products Inc. of Kingsport Tenn. was dried at 110° C. for one hour and dissolved in 300 ml dioxane. One gram pyridine was added. Three grams stearoyl chloride dissolved in 15 ml of dioxane was added dropwise and the solution was heated to 75° C. and stirred for four hours. The reaction mixture was poured into one liter of water to precipitate the polymer. The polymer was washed six times in water, filtered, and dried for two hours at 110° C.

11.0 grams of the modified film forming polymer and five grams diethylphthalate plasticizer were dissolved in 100 grams acetone. 50 ml of this solution were sprayed onto 25 grams of Monsanto Asagran 14-40 granulated aspirin in a rotating pan coater. Ten grams of the product were washed for one hour in two liters of water to remove any uncoated aspirin and the product was dried one hour in a fluid bed drier at room temperature. The results of a dissolution study are set forth in Table I below.

TABLE I

| | Dissolved Aspirin (mg) | |
|---|---|---|
| | 1 Hour | 2 Hours |
| pH 1.1 | 10.5 mg | 23.4 mg |
| pH 7.5 | 73.0 mg | 136.0 mg |

The dissolutions were performed by the U.S.P. basket dissolution method at 50 rpm in pH 1.1 and pH 7.5 buffers using a 600 mg sample. The low dissolution rate at pH 1.1 and the faster but controlled rate at pH 7.5 demonstrate the pH controlled release rate of the pharmaceutical preparation.

EXAMPLE II 750 grams cellulose acetate phthalate (Eastman C-A-P from Eastman Chemical Products. Inc., Kingsport, Tenn.) was dissolved in 3 Kg dioxane (Aldrich Chemical Company, Milwaukee, Wis.) in a four liter glass vessel fitted with a teflon paddle on a glass stirring shaft. 200 grams of stearoyl chloride (Aldrich) was added and mixed thoroughly. Subsequently, 100 ml pyridine (Aldrich) was added and the reaction was allowed to run for 12 hours at 75°-80° C. A viscous gel formed, and the gel was washed four times with water for thirty minutes in a Waring blender, then two times with 5% acetic acid. The product was dried two hours at 110° C. then placed in a vacuum dessicator for three hours.

400 grams of the product was dissolved in 3400 grams acetone. 200 grams diethylphthalate (Eastman) was added. The solution was spray coated onto 3.6 Kg chilsonated aspirin (Asagran 16/40, Monsanto Company, St. Louis, Mo.) using a Glatt GPCG-5 with a seven inch Wurster insert. 400 grams of polymer plus plasticizer was applied to the aspirin to give a 10% coating level.

This example illustrates an oral sustained release pharmaceutical preparation using the modified film forming polymer to microencapsulate a drug with a single coating. Subsequently, a dissolution study was perfomed on 600 mg of the resulting microparticles using a U.S.P.

Type I basket apparatus rotating at 50 rpm. The dissolution was run two hours in 750 ml, 0.1N HCl. 250 ml of 0.2M $Na_3PO_4$ was added to change the pH to 6.8 and then, the d was run for four more hours. The results are set forth in Table II below.

TABLE II

| Time | pH | % Dissolved |
|---|---|---|
| 1 hr. | 1.1 | 6.4% |
| 2 hrs. | 1.1 | 9.3% |
| 3 hrs. | 6.8 | 42.4% |
| 4 hrs | 6.8 | 71.0% |
| 6 hrs. | 6.8 | 96.9% |

These results illustrate again that the release rate of drug from the pharmaceutical formulation is pH controlled. That is, the percentage of aspirin dissolved at low pH (1.1) is small, and the amount of aspirin dissolved increases when the pH is raised to almost neutral (6.8).

EXAMPLE III 2500 ml of acetone was placed in a 4 liter reaction vessel and 583 g of cellulose acetate phthalate (Eastman CAp, Eastman Chemical products, Inc., Kingsport, Tenn.) was added while stirring vigorously. After all the polymer has dissolved, the solution was heated to the reflux temperature. A solution of 300 ml, 3.0N NaOH and 500 ml of acetone was added to the reaction vessel and the reaction mixture was refluxed for 6 hours. The steps described thus far is the hydrolysis procedure. Subsequently, the reaction mixture was divided into four equal parts which were all treated in the following manner.

The polymer in each part of the reaction mixture was precipitated by adding it to a blender filled with 3000 ml of 10% acetic acid and less than 1 g of antifoam (medical antifoam emulsion Dow Corning Corporation Midland, Mich.) and blending for approximately 10 seconds. The blender contents were then poured into a Buchner Funnel and suction filtered. The resulting solid was washed once with water and dried in a fluidized bed drier. All subsequent procedural steps are referred to as the esterification of the polymer.

The product designated as polymer I was prepared with one part of the hydrolyzed polymer which was added to a 4 liter reaction vessel. 300 g of dry acetone (dried using a 5% wt/vol ratio of 3 A molecular sieves) was added to the reaction vessel which was then heated to the reflux temperature. After the polymer had dissolved, a solution of 120 ml of stearoyl chloride (Aldrich Chemical Company, Milwaukee, Wis.) in 300 ml of dry acetone and 30 ml of pyridine were added to the reaction mixture. This reaction mixture was refluxed for 3 hours. Thereafter, the polymer was precipitated, filtered, washed and dried in the same manner as the hydrolysis procedure discussed above.

Prior to esterification the phthalyl content of the hydrolyzed CAP was determined by a modified NF XVI procedure for cellulose acetate phthalate described below.

The percent free phthalyl was determined by placing 3000 mg of the dry polymer in a 200 ml Erlemmeyer flask and recording the exact weight. Subsequently, 100 ml of a 1:1 methanol-water solution and a stirring bar was added to the flask. The mixture was stirred for 15 minutes and then the solids were suction filtered and washed with additional methanol-water solution. The collected liquid was then titrated with 0.1N NaOH using phenolphthalein indicator. The following formula is used to obtain the desired percentage.

$$\% \text{ free phthalyl} = \frac{8.306 \text{ (ml NaOH titrant used)}}{\text{wt. of polymer used in mg}}$$

After determining the percent free phthalyl, the percentage phthalyl attached to the polymer could be obtained. 100 mg of the polymer Was placed in a 100 ml Erlenmeyer flask along with 50 ml of acetone and a stirring bar. The mixture was stirred for 1 hour and then titrated with 0.1N NaOH using phenolphthalein indicator. The following formula was used to obtain the percentage attached phthalyl.

$$\% \text{ attached phthalyl} = \frac{1.49 \text{ (ml titrant used)} - 1.8 \text{ (\% free phthalyl)}}{100 - \% \text{ free phthalyl}}$$

The hydrolyzed cellulose acetate phthalate used to prepare polymer I had a phthalyl content of 25%.

Subsequently, the polymer was applied to drug particles using the Wurster fluidized bed process, polymer and triacetin plasticizers (Eastman) were added to acetone to make a mixture containing 8% polymer 2% plasticizer and 90% acetone. The mixture was stirred for ½ hour then passed through a 40 mesh sieve. A Glatt CPCG-5 fluid bed spray coater with a Wurster insert was used to apply the polymer to drug particles. The Glatt was kept at an inlet temperature of 40° C and the solution was sprayed immediately upon fluidizing the material to be coated at 20 g/min and increased to 60 g/min in order to keep the product temperature at 30° C. Sufficient fluidization air was used to keep the bed flowing smoothly (around 40 cfm). When spraying was completed, the line was rinsed with acetone and the coated material was dried until the product temperature rose to 34° C.

2500 g of Asagran (640 chilsonated aspirin (Monsanto Chemical Company, St. Louis, Mo.) was charged into a Wurster bowl. Subsequently, 3090 g of polymer I solution with triacetin plasticizer was sprayed onto the aspirin to produce a product with an 11% coat. The microencapsulated drug beads were analyzed using the USP method I Basket Dissolution procedure, 50 rpm, 2 hours in 0.1N HCl, 4 hours at pH. 6.8. The results of the dissolution study are set forth in Table III below.

TABLE III

| Time | Media | % Dissolved |
|------|-------|-------------|
| 1 hr. | 0.1 N HCl | 0.0% |
| 2 hrs. | 0.1 N HCl | 0.5% |
| 3 hrs. | pH 6.8 | 31.5% |
| 4 hrs | pH 6.8 | 57.2% |
| 6 hrs. | pH 6.8 | 90.3% |

The results illustrate the desired sustained-release of drug since no drug was released for 2 hours under acidic conditions, and drug was released at a constant rate for 4 hours at neutral pH. Thus the release rate of aspirin from this formulation is controlled by pH.

EXAMPLE IV

A second part of the hydrolyzed cellulose acetate phthalate of Example III was prepared in an identical manner except the reflux time during the hydrolysis reaction was reduced to 4 hours from 6 hours so as to produce a polymer with a higher phthalate content. The resulting polymer was designated as polymer II. polymer II had a phthalyl content of 28%.

Microparticles were prepared and analyzed the same as Example III except polymer II was used instead of polymer I. The results of the dissolution study are set forth in Table IV below.

TABLE IV

| Time | Media | % Dissolved |
|------|-------|-------------|
| 1 hr. | 0.1 N HCl | 0.3% |
| 2 hrs. | 0.1 N HCl | 0.8% |
| 3 hrs. | pH 6.8 | 36.3% |
| 4 hrs. | pH 6.8 | 67.8% |
| 6 hrs. | pH 6.8 | 95.2% |

These results also illustrate the desired delayed and sustained-release of drug as a result of microencapsulating the core drug with a single coat of modified film forming polymer whereby the permeability of the polymer is pH controlled. The release rate at pH 6.8 is faster for Example IV than Example III because polymer II contains more phthalate groups than polymer I. The phthalate groups become hydrophilic and increase the permeability of the membrane

EXAMPLE V

A polymer designated as polymer III was prepared by highly hydrolyzing the reaction mixture to produce a polymer with a lower phthalate content. More specifically, polymer III was produced by dissolving 500 g of cellulose acetate phthalate in 2500 ml of acetone and then adding 300 ml of 3.0N NaOH in 300 ml acetone. The reaction mixture was refluxed for 6 hours. Thereafter, heating was stopped and the reaction mixture was agitated overnight. A solution of 3.0N NaOH diluted with 300 ml acetone was added and the reaction mixture was again refluxed for 5 hours. The remainder of the polymer preparation procedure was not changed. The phthalyl content was 8.5%.

This example demonstrates the ability to adjust the release rate by varying the pH sensitive control membrane thickness. The microparticles were prepared and analyzed as in Example III, except polymer III was used as the modified film forming polymer, diethyl phthalate was substituted for triacetin, and the coating thickness was increased to 14% with a sample taken at 10%. The results are set forth in Table V below.

TABLE V

| Time | Media | % Dissolved (10% coat) | % Dissolved (14% coat) |
|------|-------|------------------------|------------------------|
| 1 hr. | 0.1 N HCl | 1.7% | 0.9% |
| 2 hrs. | 0.1 N HCl | 2.6% | 2.0% |
| 3 hrs. | pH 6.8 | 40.7% | 27.5% |
| 4 hrs | pH 6.8 | 70.0% | 50.2% |
| 6 hrs. | pH 6.8 | 99.7% | 88.1% |

Again, the results illustrate the desired delayed and sustained-release of drug as a result of the modified polymer's pH controlled permeability. Further, Table V shows that varying the coating thickness affects the dissolution rate and thus provides another means for controlling the release of drug.

EXAMPLE VI

In this example, diphenhydramine hydrochloride beads were coated with polymer III. The diphenhydramine beads were prepared by coating 25/30 mesh nonpareil seed with a diphenhydramine solution using a Wurster spray coating process to produce 80% active beads. The drug beads were coated with polymer III to a 28% coating level. The results of the dissolution study conducted on these microparticles is set forth in Table IV below.

TABLE VI

| Time | Media | % Dissolved |
|------|-------|-------------|
| 1 hr. | 0.1 N HCl | 6.5% |
| 2 hrs. | 0.1 N HCl | 12.3% |
| 3 hrs. | pH 6.8 | 65.0% |
| 4 hrs. | pH 6.8 | 79.1% |
| 6 hrs. | pH 6.8 | 97.2% |

These results illustrate that a sustained release diphenhydramine hydrochloride formulation using the modified film forming polymer has impeded release of drug under acidic conditions and also provides a substantially controlled release of drug under neutral pH conditions.

EXAMPLE VII

Eudragit NE 30D a methacrylic/acrylic acid ester copolymer from Rohm Parma GMbH of Weiterstadt, W. Ger., was used as a source of neutral methacrylic acrylic acid ester copolymer. The resin was precipitated from the dispersion by addition of 20% sodium sulfate solution. The resin was washed with water and dried in a fluidized bed at 30° C.

300 g of dry polymer was dissolved in 3 liters of acetone. 162 ml of 3.0N NaOH in 270 ml acetone was added. The solution was gently refluxed for 1 hour. The polymer was precipitated by addition of a 10% acetic acid solution, washed with water, and dried in a fluidized bed at 30° C. The resulting modified film forming polymer was approximately 12% acid groups and 88% ester groups as determined by titration of the acidic groups of a polymer sample dissolved in acetone.

A 10% solution of this modified film forming polymer in acetone was coated onto Asagran 7017 chilsonated aspirin by the Wurster process. Samples were taken at 5%, 6% and 7% coating levels. Dissolutions were performed using the USP XXI basket method at 50 rpm with a 750 mg sample. After 2 hours in 0.1N HCl the pH was increased to 6.8. The results are set forth on Table VII below.

TABLE VII

| Dissolution of Coated Aspirin | | | | |
|---|---|---|---|---|
| | Time (Hours) | | | |
| | 1 | 2 | 3 | 4 | 6 |
| 5% coat, % dissolved | 6 | 11 | 29 | 46 | 73 |
| 6% coat, % dissolved | 5 | 9 | 24 | 39 | 66 |
| 7% coat, % dissolved | 4 | 8 | 17 | 29 | 53 |
| pH | 1.1 | 1.1 | 6.8 | 6.8 | 6.8 |

As can be seen in the dissolution rate of the aspirin at a low pH was low. Increasing the pH caused the dissolution rate to increase and the aspirin was released in a controlled manner with the rate dependent on the coating level.

EXAMPLE VIII

A modified film forming polymer was prepared as in example VII except 54 ml of 3.0N MaOH was used instead of 162 ml. This polymer contained approximately 4% acid groups and 96% ester groups. The polymer was applied to Aspirin by the same procedure as in example X. The dissolution was also performed as in example X. The results are set forth in Table VIII below.

TABLE VIII

| Dissolution of Coated Aspirin, Example 2 | | | | |
|---|---|---|---|---|
| | Time (Hours) | | | |
| | 1 | 2 | 3 | 4 | 6 |
| 5% Coat, % dissolved | 5 | 10 | 18 | 25 | 38 |
| pH | 1.1 | 1.1 | 6.8 | 6.8 | 6.8 |

The results show that only a slight increase in dissolution rate occurs when the pH is increased. Since the polymer of this example contains fewer acid groups than the polymer of example VII, the increase in hydrophilicity and permeability with the increase in pH is less.

EXAMPLE IX 150 g of dry neutral methacrylic/acrylic acid ester polymer from Example VII were dissolved in 3 liters of acetone. 162 ml of 3N NaOH was added and the solution was refluxed for 2.5 hours. The product was precipitated, washed, and dried. The resulting modified film forming polymer contained approximately 23% acid groups and 77% ester groups. The modified film forming polymer was dissolved in acetone and cast into a film on a glass plate. The film was placed in 0.1N HCl and pH 6.8 phosphate buffer. The film remained intact for over 6 hours.

This example illustrates the concept of modified film forming polymers which form diffusion barriers with low permeability at gastric pH but have higher permeability at intestinal pH. Any acrylic acid polymer, methacrylic acid polymer, or acrylic/methacrylic acid copolymer containing a balance of ester groups and acid groups such that the polymer forms a film of low permeability at gastric pH but has a higher permeability yet remains intact at intestinal pH may be used. A further example is set forth in Example XIII which follows.

EXAMPLE X

The dry neutral methacrylic/acrylic acid ester polymer of Example VII was partially hydrolyzed as in example IX except a reflux time of 3 hours was used. The resulting modified film forming polymer had approximately 26% acid groups and 74% ester groups. A film of this polymer was prepared as in example XII. This film did not dissolve in 0.1N HCl but began to disintegrate after 6 hours in pH 6.8 phosphate buffer. This example illustrates that if the acid content of the polymer is too high the polymer will not form a diffusion barrier which remains intact at intestinal pH.

While the product and method herein described constitute preferred embodiments of the invention, it is to be understood that the invention is not limited to this precise product and method, and that changes may be made therein without departing from the scope of the invention.

What is claimed is:

1. A sustained-release pharmaceutical preparation comprising multi-units of microparticles comprising:
   (a) a granular core containing a water soluble drug,
   (b) a pH controlled diffusion membrane surrounding said core drug, said pH controlled diffusion membrane being formed from a film forming polymer comprising hydrophobic side chains attached to an enteric polymer which results in said film forming polymer being hydrophobic at pH range as found in the stomach and hydrophilic at pH range as found in the intestines, while said pH controlled diffusion membrane remains intact at pH range as found in the intestines.

2. The sustained-release pharmaceutical preparation of claim 1 wherein said core drug is selected from the group consisting of aspirin, acetaminophen, diphenhydramine hydrochloride, propranolol hydrochloride, dextromethorphan hydrobromide, disopyramide phosphate and furosemide.

3. The sustained-release pharmacetical preparation of claim 2 wherein said enteric polymer is selected from the group consisting of cellulose acetate phthalate, cellulose acetate trimellitate, hydroxypropylmethyl cellulose phthalate, polyvinyl acetate phthalate, hydroxyethylethyl cellulose phthalate and cellulose acetate tetrahydrophthalate.

4. The sustained-release pharmaceutical preparation of claim 3 wherein said enteric polymer is cellulose acetate phthalate.

5. The sustained-release pharmaceutical preparation of claim 4 wherein said hydrophobic side chain is a stearyl side chain formed by esterifying hydroxyl groups on the cellulose acetate phthalate with stearoyl chloride.

6. The sustained-release pharmaceutical preparation of claim 1 further including free drug or time-release drug.

7. The sustained-release pharmaceutical preparation of claim 6 wherein said free drug or time-release drug is admixed with said microparticles.

8. The sustained-release pharmaceutical preparation of claim 6 wherein said free drug or time-release drug is concentrically coated on said microparticles.

9. The sustained-release pharmaceutical preparation of claim 1 wherein said microparticles are around 110 to 2200 microns in diameter.

10. The sustained-release pharmaceutical preparation of claim 7 wherein said core drug is in the form of particles about 100 to 2000 microns in diameter, said pH controlled diffusion membrane is about 5 to 100 microns thick.

11. The sustained-release pharmaceutical preparation of claim 1 wherein said pH controlled diffusion membrane releases 0–15% of said core drug at pH 1.1 in 2 hours and 80-100% of said core drug at pH 6.0-7.5 in 6-24 hours.

12. A sustained-release pharmaceutical preparation comprising multi-units of microparticles comprising:
   (a) a granular core containing a water soluble drug,
   (b) a pH controlled diffusion membrane surrounding said core drug, said pH controlled diffusion membrane being formed from a film forming polymer comprising a first set of subunits which are hydrophobic to keep said pH controlled diffusion membrane intact at pH range as found in the intestines and a second set of subunits which contain free acid groups so that said film forming polymer is hydrophobic at pH range as found in the stomach and hydrophilic at pH range as found in the intestines.

13. The sustained-release pharmaceutical preparation of claim 12 wherein said core drug is selected from the group consisting of aspirin, acetaminophen, diphenhydramine hydrochloride, propranolol hydrochloride, dextromethorphan hydrobromide, disopyramide phosphate and furosemide.

14. The sustained-release pharmaceutical preparation of claim 12 further including free drug or time-release drug.

15. The sustained-release pharmaceutical preparation of claim 12 wherein said film forming polymer is selected from the group consisting of methacrylic/acrylic acid/ester copolymers, polyethylene maleic anhydride, and polystyrene maleic anhydride.

16. The sustained-release pharmaceutical preparation of claim 12 wherein said film forming polymer is a methacrylic/acrylic acid ester copolymer.

17. The sustained-release pharmaceutical preparation of claim 14 wherein said free drug or time-release drug is admixed with said microparticles.

18. The sustained-release pharmaceutical preparation of claim 13 wherein said free drug or time-release drug is concentrically coated on said microparticles.

19. The sustained-release pharmaceutical preparation of claim 12 wherein said microparticles are around 110 to 2200 microns in diameter.

20. The sustained-release pharmaceutical preparation of claim 19 wherein said core drug is in the form of particles about 100 to 2000 microns in diameter, said pH controlled diffusion membrane is about 5 to 100 microns thick.

21. The sustained-release pharmaceutical preparation of claim 12 wherein said pH controlled diffusion membrane release 0-15% of said core drug at pH 1.1 in 2 hours and 80-100% of said core drug at pH 6.0-7.5 in 6-24 hours.

22. A sustained-release pharmaceutical preparation comprising multi-units of microparticles comprising:
   (a) a granular core containing a water soluble drug, said water soluble drug selected from the group consisting of aspirin, acetaminophen, diphenhydramine hydrochloride, propranolol hydrochloride, dextromethorphan hydrobromide, disopyramide phosphate and furosemide,
   (b) a pH controlled diffusion membrane surrounding said core drug, said pH controlled diffusion membrane being formed from a film forming polymer comprising hydrophobic stearyl side chains attached to an enteric polymer which results in said film forming polymer being hydrophobic at pH range as found in the stomach and hydrophilic at neutral and alkaline pH as found in the intestines, while said pH controlled diffusion membrane remains intact at neutral and alkaline pH as found in the intestines.

23. A sustained-release pharmaceutical preparation comprising multi-units of microparticles comprising:
   (a) a granular core containing a water soluble drug, said water soluble drug selected from the group consisting of aspirin, acetaminophen, diphenhydramine hydrochloride, propranolol hydrochloride, dextromethorphan hydrobromide, disopyramide phosphate and furosemide,
   (b) a pH controlled diffusion membrane surrounding said core drug, said pH controlled diffusion membrane being formed from a methacrylic/acrylic acid ester copolymer.

* * * * *

UNITED STATES PATENT AND TRADEMARK OFFICE
CERTIFICATE OF CORRECTION

PATENT NO. : 4,983,401

DATED : January 8, 1991

INVENTOR(S) : Herman J. Eichel; Brent D. Massmann

It is certified that error appears in the above-identified patent and that said Letters Patent is hereby corrected as shown below:

Title Page:
Abstract, Line 18: "coated into core drug" should be --coated onto core drug--.
Col. 3, Line 34, "polymers mav" should be --polymers may--.
Col. 7, Line 23, "the d was" should be --the dissolution was--.
Col. 10, Line 52, "3.ON" should be --3.0$\underline{N}$--.
Col. 10, Line 66, "O.1N" should be --0.1$\underline{N}$--.
Col. 11, Line 18, "3.ON" should be --3.0$\underline{N}$--.
Col. 11, Line 43, "3N" should be --3$\underline{N}$--.
Col. 11, Line 49, "O.1N" should be --0.1$\underline{N}$--.
Col. 12, Line 2, "O.1N" should be --0.1$\underline{N}$--.
Col. 12, Line 62, "claim 7" should be --claim 9--.
Col. 14, Line 26, "neutral and alkaline pH as" should be --pH range--.
Line 28, "at neutral and alkaline pH" should be --at pH range--.

Signed and Sealed this

Twentieth Day of October, 1992

Attest:

DOUGLAS B. COMER

*Attesting Officer*  *Acting Commissioner of Patents and Trademarks*